(12) United States Patent
Shimazaki

(10) Patent No.: US 7,295,294 B2
(45) Date of Patent: Nov. 13, 2007

(54) OPTICAL WAVEGUIDE SENSOR AND MEASURING APPARATUS USING SAID OPTICAL WAVEGUIDE SENSOR, AND MEASURING METHOD USING A SENSOR

(75) Inventor: Takaaki Shimazaki, Kyoto (JP)

(73) Assignee: Rohm Co., Ltd. (JP)

( * ) Notice: Subject to any disclaimer, the term of this patent is extended or adjusted under 35 U.S.C. 154(b) by 312 days.

(21) Appl. No.: 10/974,215

(22) Filed: Oct. 27, 2004

(65) Prior Publication Data

US 2005/0089261 A1 Apr. 28, 2005

(30) Foreign Application Priority Data

Oct. 28, 2003 (JP) ............... 2003-367201

(51) Int. Cl.
*G01N 21/27* (2006.01)
(52) U.S. Cl. ................... 356/128; 265/445; 422/82.11; 250/227.14; 385/12
(58) Field of Classification Search ............... 356/128, 356/445; 385/12, 50; 250/227.14; 422/82.11
See application file for complete search history.

(56) References Cited

U.S. PATENT DOCUMENTS

| | | | | |
|---|---|---|---|---|
| 5,173,747 A | * | 12/1992 | Boiarski et al. | ............ 356/481 |
| 5,377,008 A | * | 12/1994 | Ridgway et al. | ............ 356/481 |
| 6,442,319 B1 | | 8/2002 | Dietz et al. | |
| 2002/0172457 A1 | | 11/2002 | Tapalian et al. | |
| 2004/0081384 A1 | * | 4/2004 | Datesman et al. | ............ 385/12 |

FOREIGN PATENT DOCUMENTS

| | | |
|---|---|---|
| DE | 3415242 C1 | 10/1985 |
| JP | 08-075639 | 3/1996 |
| JP | 2002-148187 | 5/2002 |

OTHER PUBLICATIONS

European Search Report for Application No. 04256666.1-2204 dated Jan. 21, 2005.
Krioukov, E. et al. "Performance of integrated optical microcavities for refractive index and fluorescence sensing", Sensors and Actuators B, Apr. 20, 2003, pp. 58-67.
Hua, P. et al. "Integrated optical dual Mach-Zehnder interferometer sensor", Sensors and Actuators B, Dec. 10, 2002, pp. 250-257.
Drapp, B. et al. "Integrated optical Mach-Zehnder interferometers as simazine immunoprobes", Sensors and Actuators B, Mar. 1997, pp. 277-282.

(Continued)

*Primary Examiner*—Richard A. Rosenberger
(74) *Attorney, Agent, or Firm*—Cantor Colburn LLP

(57) ABSTRACT

A first core layer and a second core layer, serving as optical waveguides, whose refractive indexes are greater than that of a substrate are placed on the surface of the substrate that functions as a cladding layer. An interval between the first core layer and the second core layer is partially narrowed so that lightwaves progressing through these core layers may develop an optical mode coupling. Disposed in this optical mode coupling area is a detector, which comes in contact with liquid or gas and interacts with a substance to be detected, such as chemical or biological substance. A receptor material which selectively captures the substance to be detected is fixed on a surface of the detector. Antibody, enzyme, cell, ionophore, single-strand DNA and the like are examples of the receptor material.

15 Claims, 14 Drawing Sheets

OTHER PUBLICATIONS

Harris, R.D. et al. "Waveguide surface plasmon resonance sensors", Sensors and Actuators B, Oct. 1995, pp. 261-267.

European Office Action for Application No. 04-256 666.1-2204 mailed Jan. 18, 2007.

* cited by examiner

100

OPTICAL WAVEGUIDE SENSOR AND MEASURING APPARATUS USING SAID OPTICAL WAVEGUIDE SENSOR, AND MEASURING METHOD USING A SENSOR

BACKGROUND OF THE INVENTION

1. Field of the Invention

The present invention relates to optical waveguide sensors utilizing the optical mode coupling, measuring apparatus using the optical waveguide sensor and measuring method using a sensor.

2. Description of the Related Art

In recent years, technologies for detecting and quantitating chemical substances, such as ammonium ion or sodium ion, or biological substances, such as DNA or antigen antibody, have been growing in importance in the areas of medical care, health, food, development of new drugs, chemistry and biochemistry. In particular, a number of proposals have been made of optical waveguide sensors capable of detecting and quantitating ultramicro amounts of substance with high sensitivity, high speed and simplicity by making use of the interaction between substance present on an optical waveguide and lightwaves (see, for example, Reference (1) or Reference (2) in the following Related Art List).

Related Art List
(1) Japanese Patent Application Laid-Open No. Hei8-75639.
(2) Japanese Patent Application Laid-Open No. 2002-148187.

These optical waveguide sensors operate, using the change in absorptance of lightwaves caused by the acquisition of substance to be detected or the change in surface plasmon resonance state caused by the acquisition of substance to be detected.

The former type of optical waveguide sensor is comprised of a cladding layer made of light transmitting material and a single line of core layer whose refractive index is larger than that of the cladding layer. The cladding layer has a function of confining light by enclosing part of the core layer, and the core layer has a function of a waveguide through which lightwaves propagate while undergoing total reflection. The part of the core layer which is not enclosed by the cladding layer is in contact with liquid or gas containing the substance to be detected. Of the lightwaves led into the core layer, only the lightwaves having the angle of incidence and wave number that satisfy an eigenvalue equation propagate while undergoing total reflection. At this time, the evanescent waves extend about the length of one wave outside the core layer. If there is any change in the mass of the substance to be detected within the range of the evanescent waves, there will be a change in the absorbed amount of lightwaves of a specific wavelength corresponding to the substance. With white light (multi-wavelength light) used as incident wave, the type and amount of detected substance are known from the spectrum distribution of the output waves.

The latter type of optical waveguide sensor is an optical waveguide type surface plasmon resonance sensor wherein a metal thin film with receptors attached thereon is so disposed on the core layer that it comes in contact with liquid or gas containing the substance to be detected. The lightwaves propagated through the core layer, which are incident on the lower surface of the metal thin layer under total reflection conditions, ooze out once to the upper surface of the conductive thin film and become the evanescent waves. At this point, when the wave number of the evanescent waves originating in p polarization agrees with that of the surface plasmon, a resonance occurs, thus transforming the incident wave energy into the resonance energy and nearly zeroing the reflected wave energy. This is called a surface plasmon resonance.

Here, the wave number of surface plasmon is defined by the complex dielectric constant (or complex refractive index, and hereinafter "dielectric constant" and "refractive index" will be used as equivalents) of conducting thin film, the dielectric constant of a reaction area, and the wavelength of the surface plasmon. The wave number of the evanescent waves is defined by the dielectric constant of the core layer and the wavelength and the angle of incidence of the incident waves.

The lightwaves, which are white light (multi-wavelength light), contain diverse wavelengths and diverse angles of incidence corresponding thereto. Only the energy of lightwaves that have the wavelength and angle of incidence satisfying the resonance conditions is consumed as the resonance energy, so that it is possible to identify the type and amount of detected substance to be detected from the spectrum distribution of the output waves.

Known technologies, however, have inherent problems. That is, the lightwaves to be propagated through the core layer must be white light (multi-wavelength light) in order to determine the type and amount of substance to be detected from a spectrum. This results in a large source of light and measuring equipment.

Moreover, the length of the waveguide must be long if the sensitivity is to be raised. This results in a large-size detector.

Moreover, the energy absorbed of the incident wave energy is very small, and the necessity for measuring a small change in a large signal results in the problem of low accuracy of measurement.

SUMMARY OF THE INVENTION

The present invention has been made in view of the foregoing circumstances and an object thereof is to achieve small size and high accuracy for a measuring apparatus.

A first optical waveguide sensor according to the present invention, includes: a first waveguide having an inlet end for incoming light; a second waveguide having an exit end for detecting light; and an optical coupling area where said first waveguide and said second waveguide are positioned within a predetermined interval therebetween, wherein in the optical coupling area there is provided a detector, disposed between the first waveguide and the second waveguide, which interacts with a substance to be detected.

In this sensor, the incoming light is led to the first waveguide. Part of the incoming light shifts to the second waveguide. A shifted amount of light varies according to the presence or absence of the substance to be detected, so that the light extracted from the exit end of the second waveguide is measured as the detecting light.

A detector is provided in the optical coupling area. The detector interacts with the substance to be detected and, as a result, a coupling state of light in the optical coupling area varies. That is, when there is a substance to be detected, the shifted amount of light from the first waveguide to the second waveguide changes. Thus, the substance to be detected can be analyzed by measuring an amount of outgoing light from the second waveguide.

With this sensor, the light shifted to the second waveguide is to be measured unlike in the conventional measuring equipment where the measurement is carried out by detecting a small change in the incoming light of high intensity. Thus, favorable measurements with high S/N ratio can be obtained. Moreover, since the measurement sensitivity is high, a short and small optical coupling area suffices and, therefore, the measuring apparatus can be made smaller. Moreover, since it is possible in principle that measurement can be done by the light of a single wavelength, there is no need of using white light as in the conventional SPR sensor. Thus, the apparatus can be made smaller.

A second optical waveguide sensor according to the present invention, includes: a first waveguide having an inlet end for incoming light; a second waveguide having an exit end for detecting light; an optical coupling area where said first waveguide and said second waveguide are positioned within a predetermined interval therebetween; and a detector, interacting with a substance to be detected, which is positioned in the close proximity of the first waveguide and is located within an area covered from the inlet end up to the optical coupling area.

In this sensor, the incoming light is led to the first waveguide. Part of the incoming light shifts to the second waveguide. A shifted amount of light varies according to the presence or absence of the substance to be detected, so that the light extracted from the exit end of the second waveguide is measured as the detecting light.

The detector is provided in the close proximity of the first waveguide and is located within an area covered from the inlet end up to the optical coupling area. The detector interacts with a substance to be detected. Thereby, a lost amount of light in the optical coupling area changes. Thus, if substance to be detected is present, a shifted amount of light from the first waveguide to the second waveguide will change. Then, the substance to be detected can be analyzed by measuring an amount of outgoing light from the second waveguide.

With this sensor, the light shifted to the second waveguide is to be measured unlike in the conventional measuring equipment where the measurement is carried out by detecting a small change in the incoming light of high intensity. Thus, favorable measurements with high S/N ratio can be obtained. Moreover, since the measurement sensitivity is high, a short and small optical coupling area suffices and, therefore, the measuring apparatus can be made smaller. Moreover, since it is possible in principle that measurement can be done by the light of a single wavelength, there is no need of using white light as in the conventional SPR sensor. Thus, the apparatus can be made smaller.

In the second optical waveguide sensor, a structure may be such that the detector contains metal film. By employing this structure, it is possible to carry out a measurement utilizing a change in a state of the surface plasmon resonance, so that the apparatus can be made smaller and the measurement can be made with high accuracy.

The detector according to the present invention may be structured such that a receptor material which selectively captures substance to be detected is disposed on a surface of the detector. By implementing this structure, the substance to be detected can be measured in a sensitive manner. Moreover, there may be provided a plurality of detectors and a plurality of different receptor materials may be placed on the respective plurality of detectors. By implementing this structure, a plurality of substances to be detected can be measured quickly and accurately.

The method for introducing a sample may be any of a method of dropping sample solution, a method in which a flow cell with an exposed detector is provided and sample solution flows through this cell, and others. For example, a structure may be such that there is provided a flow path in contact with the detector and a surface of the detector is exposed on this flow path. By employing this structure, the introduction of sample becomes simplified, so that a plurality of substance to be detected can be measured quickly and accurately.

According to the present invention, there is provided a measuring apparatus equipped with the above-described sensor. That is, there is provided a measuring apparatus which includes: a bodily fluid collecting unit; a sensor which analyzes bodily fluid collected by the bodily fluid collecting unit; and a flow path which introduces the bodily fluid from the bodily fluid collecting unit to the sensor, wherein the above-described optical waveguide sensor is used as a sensor and wherein the flow path is structured such that the bodily fluid is led to a detector included in the sensor.

According to this apparatus, the bodily fluid is collected and measured by the same apparatus, thus realizing quick measurement. Besides, the collected bodily fluid is measured at once, so that accurate measurement results can be obtained.

Although the structure of the present invention has been described as above, it is to be noted that any arbitrary combination of the above-described structural components, and expressions of the present invention changed between a method, a system and so forth are all effective as and encompassed by the present embodiments.

For example, according to the present invention, there may be provided an optical waveguide sensor which further includes a third waveguide having an exit end for detecting light, wherein there is further provided a detector, disposed between the first waveguide and the third waveguide, which interacts with a substance to be detected.

Moreover, according to the present invention, there is provided a measuring method in which used is a sensor having a first waveguide, a second waveguide and an optical coupling area where said first waveguide and said second waveguide are positioned within a predetermined interval therebetween, the method including: introducing incoming light in the first waveguide; introducing a sample in the optical coupling area to cause a change in a physical property, for example, the refractive index, of the optical coupling area; measuring the intensity of detecting light outputted from the second waveguide; and detecting the presence or absence of a substance to be detected or quantitating the substance by the measuring.

Moreover, according to the present invention, there is provided a measuring method in which used is a sensor having a first waveguide, a second waveguide and an optical coupling area where said first waveguide and said second waveguide are positioned within a predetermined interval therebetween, the method including: introducing incoming light in the first waveguide; introducing a sample, in an area in contact with the first waveguide between an introducing end of the incoming light and the optical coupling area, to cause a change in a physical property, for example, the refractive index, of the optical coupling area; measuring the intensity of detecting light outputted from the second waveguide; and detecting the presence or absence of a substance to be detected or quantitating the substance by the measuring.

With these measuring methods, the light to be introduced may be monochromatic light, so that the structure of the apparatus can be simplified. The light to be introduced may be a single light beam or various types of light beams.

According to the present invention described as above, adopted is a system in which a plurality of waveguides are used and the substances to be detected are analyzed by utilizing the optical mode coupling or the surface plasmon resonance, so that the measuring apparatus can be made smaller and the measurement can be done with high precision.

This summary of the invention does not necessarily describe all necessary features so that the invention may also be sub-combination of these described features.

DETAILED DESCRIPTION OF THE INVENTION

The invention will now be described based on preferred embodiments which do not intend to limit the scope of the present invention but exemplify the invention. The same reference numbers are used throughout the Figures to indicate the same or similar parts, and their repeated explanation is omitted as appropriate. All of the features and the combinations thereof described in the embodiments are not necessarily essential to the invention.

The materials to be used for the basic components, such as substrate, core layer, cladding layer and metal film, may be the same for all of the preferred embodiments of the present invention. Also, the same common structure may be used for the material usable as a receptor material and its fixing method. In each of the preferred embodiments, the method for introducing a sample may be any of a method of dropping sample solution, a method with a flow cell incorporating a detector therein through which sample solution flows, and others.

First Embodiment

Figure 1A:
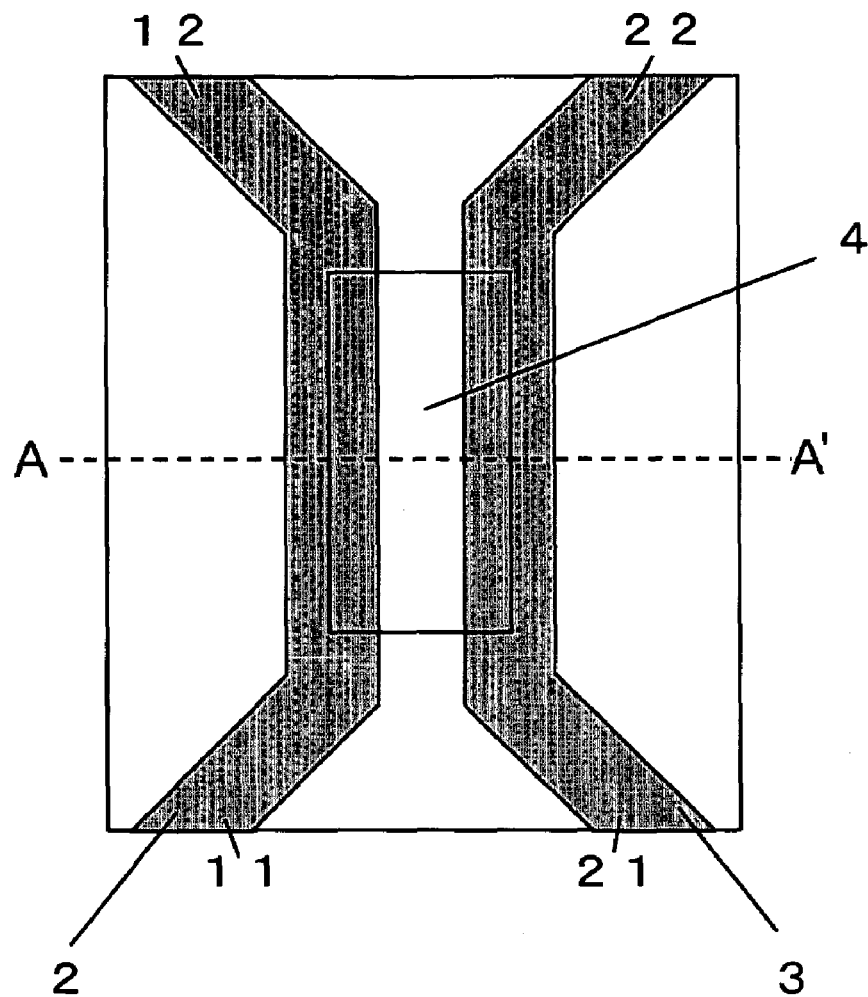
FIG. 1A and FIG. 1B illustrate schematically a structure of an optical waveguide sensor according to a first embodiment of the present invention.
Figure 1B:
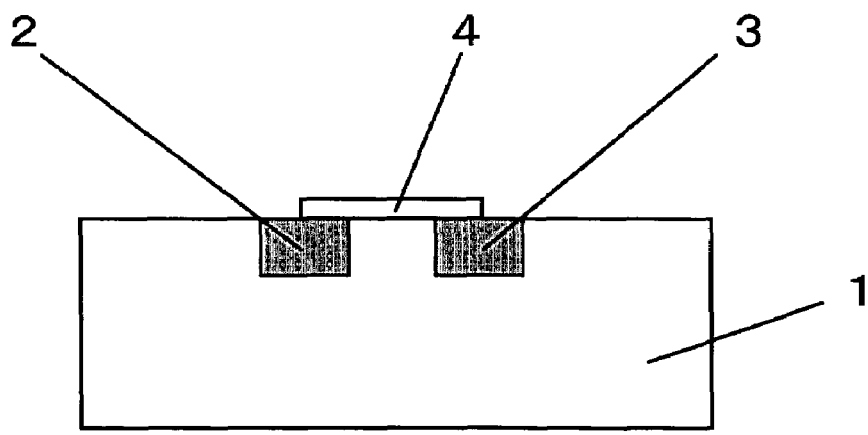

FIG. 1A and FIG. 1B illustrate schematically a structure of an optical waveguide sensor according to a first embodiment of the present invention. FIG. 1A is a top view of the sensor, and FIG. 1B is an A-A' cross-sectional view of FIG. 1A. Disposed on the surface of a substrate 1, which functions as a cladding layer, are a first core layer 2 and a second core layer 3, which have a larger refractive index than the substrate 1 and serve as an optical waveguide.

As material for the substrate 1, epoxy (refractive index: 1.43-1.62) or acryl (refractive index: 1.33-1.70) may be used.

As a material for the first core layer 2 and the second core layer 3, any of the PMMA type, polycarbonate type, deuterated polymer type, fluorinated polymer type, norbornen type, polystyrene type or silicone polymer type materials may be used. In addition to these, an optical glass such as BK7 or F2 may be used.

The interval between the first core layer 2 and the second core layer 3 is partially narrowed so that lightwaves progressing therethrough may develop an optical mode coupling. Disposed in the area of this optical mode coupling is a detector 4, which comes in contact with liquid or gas and interacts with a substance to be detected, such as chemical or biological substance.

The detector 4 is an area where a predetermined receptor material is fixed on the surface of the substrate 1, the first core layer 2 and the second core layer 3. In the present embodiment, the receptor material used is such material as to change the refractive index of the detector 4 when it captures substance to be detected. The mode of capturing, which is subject to no particular limitations, may be adsorption or bonding. As these receptor materials there may be a receptor such as antibody, enzyme, cell, ionophore or single-strand DNA. The combination of a receptor material and a substance to be detected may be any of various sorts of ligand-receptor combinations. Such examples of the combination include antigen vs. antibody, enzyme vs. substrate or reaction inhibitor, hormone vs. hormone receptor, polynucleotide vs. complementary polynucleotide, protein A vs. immunoglobulin, and lectin vs. specific carbohydrate combinations. And in each of the combinations, one may be used as the receptor material and the other as the substance to be detected.

The receptor material may be fixed to the detector 4 using any of a variety of methods. For example, after forming a coating layer of carboxymethyldextran on a ground (the surfaces of the substrate 1, the first core layer 2 and the second core layer 3 in the present embodiment) directly or via a linker layer, the carboxyl group can be activated by the use of carbodiimide and then a predetermined receptor material can be bonded with dextran through the agency of the carboxyl group. In addition, it is possible to fix a dextran layer using an electrostatic interaction. For example, when fixing a dextran layer on a plastic, dextran can be adsorbed by an electrostatic interaction, using a cationic PDDA (polydiallyldimethylammonium chloride) or an anionic PVS (polyvinyl potassium sulfate). More specifically, a dextran layer is negatively charged in a basic solution whose pH is higher than 7 and at the same time the surface of the plastic is negatively charged by a plasma processing, so that the dextran layer can be fixed on the plastic surface by the agency of the cationic PDDA or PVS.

As another method for fixing a receptor material to the detector 4, biotin-avidin bond may be used. After forming a coating layer of streptoavidin on the ground (the surfaces of the substrate 1, the first core layer 2 and the second core layer 3 in the present embodiment) directly or via a linker layer, biotinylated receptor material can be introduced and it may be fixed.

Now the principle of operation of a sensor as shown in FIGS. 1A and 1B will be described. First, lightwaves are sent in from an end 11 of a first core layer 2. The lightwaves that progress through the first core layer 2 have the angle of incidence and wave number that satisfy an eigenvalue equation and are propagated therethrough while undergoing total reflection. At this time, parts of the lightwaves are propagated as evanescent waves that have oozed out of the first core layer 2. When the evanescent waves reach the second core layer 3, an optical mode coupling takes place wherein part of the energy of lightwaves advancing through the first core layer 2 shifts to the second core layer 3. This is the same principle of operation as with a directional coupler.

When the interval between the first core layer 2 and the second core layer 3 becomes approximately $1/\gamma$ or below, a strong optical mode coupling occurs. $1/\gamma$ is an amount equal to the length of the oozing out of the evanescent waves, and $\gamma$ is expressed by $$\gamma = (\beta_0^2 - k_0^2 n_3^2)^{1/2}$$

where $\beta_0$ is a propagation constant of lightwaves advancing through the first core layer 2 when it exists alone, $k_0$ is the wave number of lightwaves advancing through the first core layer 2, and $n_3$ is the refractive index in the intermediate area between the first core layer 2 and the second core layer 3. The "intermediate area" meant here is the area between the two waveguides (core layers) which affects the optical mode coupling.

A coupling coefficient K at this time is expressed as $$K = (\kappa_0^2 \times \epsilon^{-\gamma d})/[\beta_0 \times \gamma a \times \{1 + (\kappa_0/\gamma)\}^2]$$

where d is the interval between the first core layer 2 and the second core layer 3, $\kappa_0$ is a quantity determined by $\beta_0$ and the refractive index of the first core layer 2, and a is the width of the first core layer 2 and the second core layer 3.

Moreover, if the standardized lightwave energies of the first core layer 2 and the second core layer 3 are to be a(L) and b(L), respectively, then the following relations will hold:

$$|a(L)|^2 = 1 - |b(L)|^2$$

$$|b(L)|^2 = \sin^2(KL)$$

where L represents the length of an optical mode coupling area in the lightwave traveling direction. It is to be noted here that the first core layer 2 and the second core layer 3 are treated as equivalents in these expressions.

As described above, the lightwaves sent in from the end 11 of the first core layer 2 shift to the second core layer 3 in the optical mode coupling area in a manner dependent on the refractive index of the intermediate area between the first core layer 2 and the second core layer 3 and are outputted from another end 22.

A sensor according to the present embodiment utilizes the dependence of optical mode coupling on the refractive index of a detector 4 placed in the intermediate area between the first core layer 2 and the second core layer 3. That is, the refractive index of the detector 4 is obtained by measuring the lightwave energies at the end 11 and the end 22, and the detection and quantitation of the substance to be detected are carried out at the detector 4.

Figure 2:
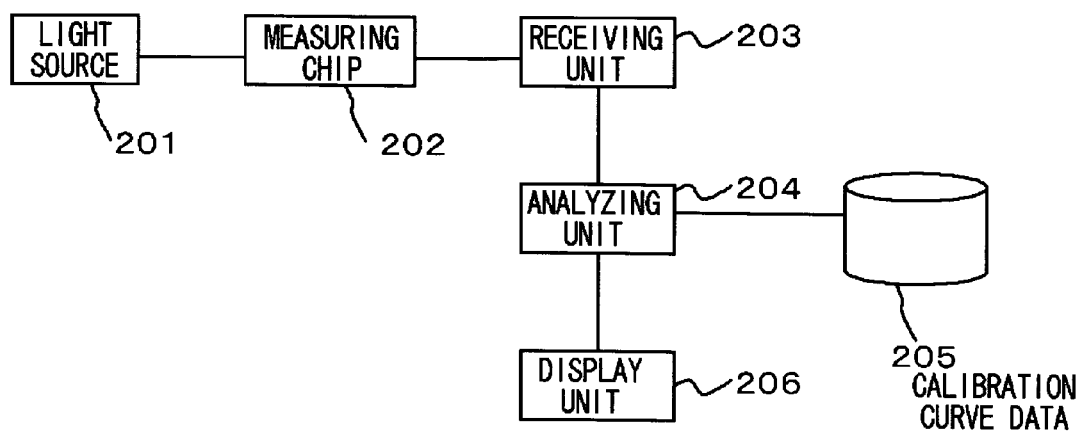
FIG. 2 illustrates an overall structure of a measuring apparatus using a sensor of FIG. 1A and FIG. 1B as a measuring chip.

FIG. 2 is illustrates an overall structure of a measuring apparatus using a sensor of FIGS. 1A and 1B as a measuring chip. Incoming light beam emitted by a light source 201 is led to a measuring chip 202. Detecting light is emitted from the measuring chip 202 and received by a receiving unit 203.

As the light source 201, a semiconductor laser or the like may be used. The wavelength of the laser may be selected to suit the purpose. For example, a semiconductor laser may be used that can emit light beam whose wavelength are 1.55 μm, 1.3 μm and so forth. As the receiving unit 203, a silicon photodiode or the like may be used.

For example, the relationship between the strength of detecting light and the refractive index and the relationship between the refractive index and the concentration of the substance to be detected are determined beforehand by experiment or simulation, and they are stored as calibration curve data 205.

An analyzing unit 204 not only acquires the intensity of light received by the receiving unit 203 but also performs a quantitative analysis of a sample to be measured, by comparing it with the calibration curve data 205. The result is displayed by a display unit 206.

Conventionally, a substance is detected and quantitated from the change in the absorbed amount of light or the state of surface plasmon resonance when the substance to be detected is captured by a single waveguide. With a sensor according to the present embodiment, however, a substance is detected and quantitated by the use of optical mode coupling dependent on the refractive index that changes when the substance to be detected is captured by a plurality of waveguides. Thus, the method and apparatus according to the present embodiment presents an advantage of analyzing minute quantities of substance with high accuracy. It can also make the equipment smaller by enabling measurement with monochromatic light. Furthermore, measurements with high S/N ratio can be obtained.

The following is a supplementary explanation of why the use of a plurality of waveguides improves the S/N ratio. Referring to the sensor shown in FIGS. 1A and 1B, if the incident light energy entering from the end 11 is $E_0$ and the energy absorbed at the detector 4 is $E_1$, then the measurement at the end 12 will be such that the optical output energy when there is no substance to be detected is $E_0$ and the optical output energy when there is substance to be detected is $(E_0 - E_1)$. And these are compared to perform an analysis of the receptor material. On the other hand, in the measurement at the end 22, the optical output energy, when there is no substance to be detected, will be $\alpha E_0$ if the factor affecting the optical mode coupling is $\alpha$. And when there is substance to be detected, the optical output energy will be $\beta \alpha E_0$ if the effect of the change in refractive index on the optical mode coupling is $\beta$. And these are compared to perform an analysis of the receptor material. Generally speaking, $E_0 \gg E_1$, and therefore it is extremely difficult for the measurement at the end 12, wherein large signal $E_0$ and very small signal $E_1$ must be detected with the same measuring device, to measure with a high S/N ratio. On the other hand, in the measurement at the end 22, the measuring range may be compressed $\alpha$ ($<1$) times by $\alpha$, which can be set by the form of the intermediate area, so that it is possible to measure with a higher S/N ratio using a receiving unit with higher sensitivity in a narrow range.

Figure 3A:
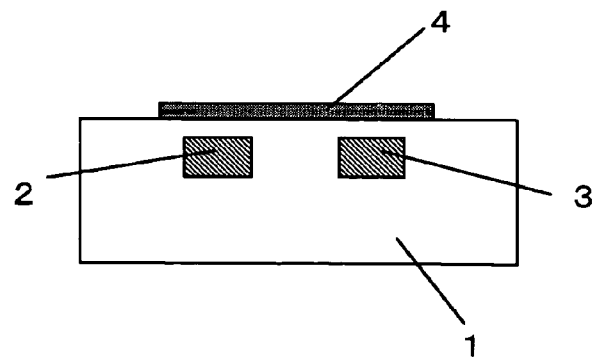
FIGS. 3A to 3D illustrate various modes in which core layers and cladding layers are disposed.
Figure 3B:
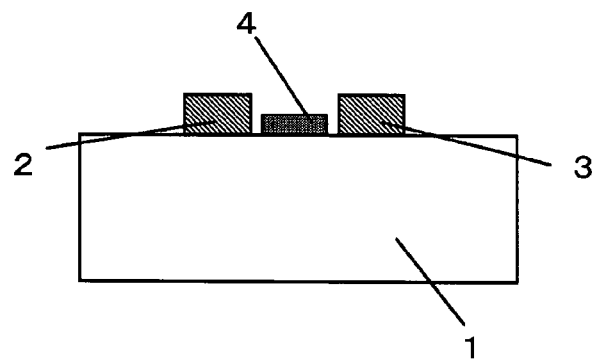
Figure 3C:
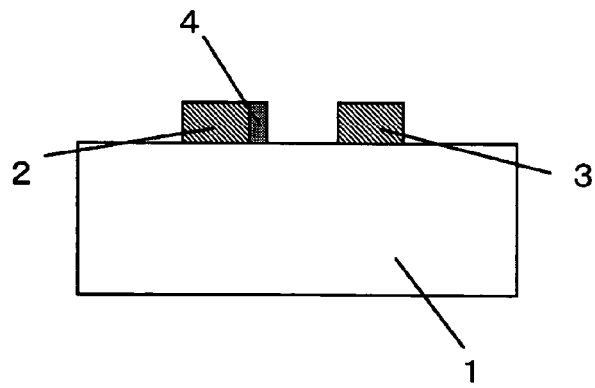
Figure 3D:
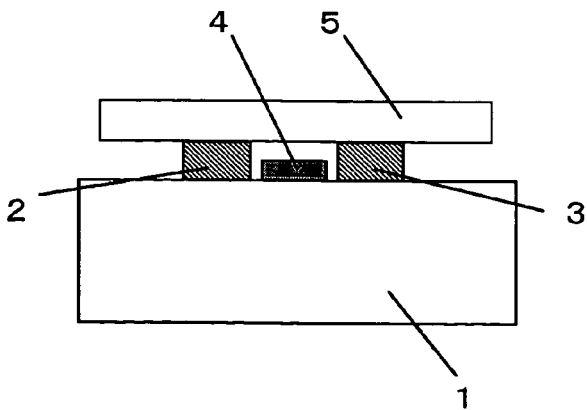

FIGS. 3A to 3D illustrate various modes in which core layers and cladding layers are disposed. A first core layer 2 and a second core layer 3 may be disposed either inside a substrate 1 (FIG. 3A) or exposed on the top surface of the substrate 1 (FIG. 3B). Moreover, a detector 4 may be present in any part of the intermediate area between the first core layer 2 and the second core layer 3 (FIG. 3C). Furthermore, a second cladding layer 5 may be provided on top of the first core layer 2 and the second core layer 3, so that a flow-type optical waveform sensor may be formed in which liquid or gas containing a substance to be detected flows between the first core layer 2 and the second core layer 3 (FIG. 3D) According to this embodiment, performed are a step of introducing incoming light beam in the first core layer 2, a step of introducing a sample in the optical mode coupling area to cause a change in the physical properties (refractive index) of the optical mode coupling area, and a step of measuring the intensity of detecting light outputted from the second core layer 3. And by the measurement of the intensity of this detecting light, the presence or absence of substance to be detected in the sample is determined and, if determined present, the substance is quantitated.

Second Embodiment

A second embodiment concerns an optical waveguide sensor utilizing surface plasmon resonance and optical mode coupling.

Figure 4A:
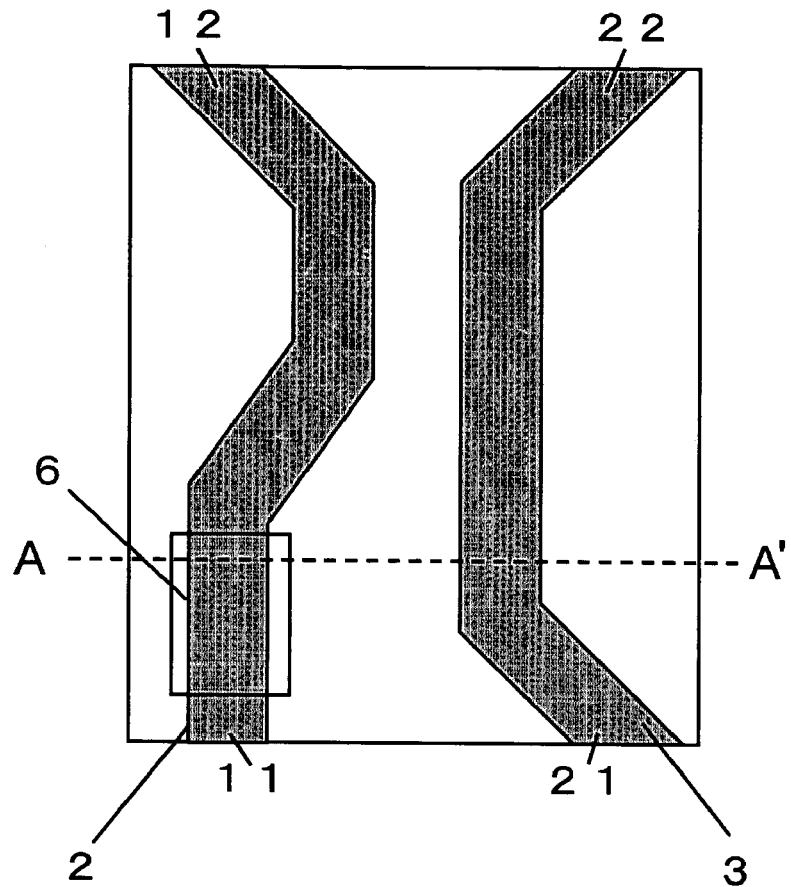
FIG. 4A and FIG. 4B illustrate schematically a structure of an optical waveguide sensor according to a second embodiment of the present invention.
Figure 4B:
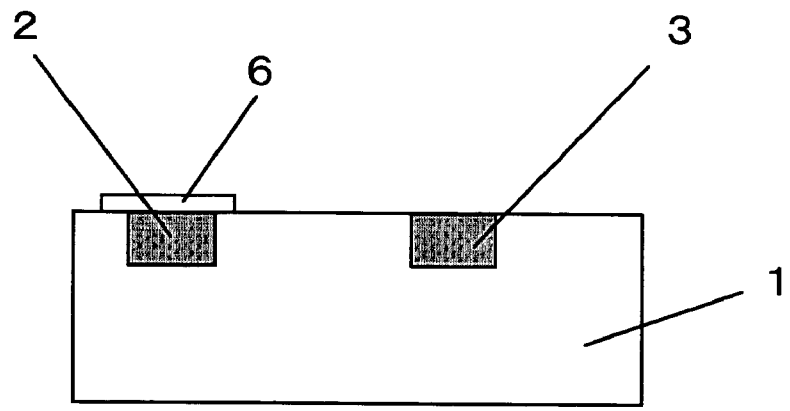

FIG. 4A and FIG. 4B illustrate schematically a structure of an optical waveguide sensor according to a second embodiment of the present invention. FIG. 4A is a top view of the sensor, and FIG. 4B is an A-A' cross-sectional view of FIG. 4A. The second embodiment differs from the first embodiment in that a detector 6 is disposed on top of a first core layer 2. The detector 6 is of such a structure that a receptor material, which develops an interaction with a substance to be detected, adheres to a metal thin film. As material for the metal film, a metallic material that produces surface plasmon, such as gold, silver or aluminum, is preferably used. The material usable as a receptor material and its fixing method are the same as described in the first embodiment.

Now the principle of operation of this sensor will be described. First, lightwaves are sent in from an end 11 of a first core layer 2. The lightwaves that travel through the first core layer 2 have the angle of incidence and wave number that satisfy an eigenvalue equation and are propagated therethrough while undergoing total reflection. If the dimensions and the refractive index of the first core layer 2 and the wavelength of the lightwaves advancing therethrough are properly set, then the evanescent waves of the lightwaves propagated while undergoing total reflection and the surface plasmon will have the same wave number, thus causing a surface plasmon resonance.

On the other hand, part of the lightwaves are propagated as evanescent waves that have oozed out of the first core layer 2. When these evanescent waves reach the second core layer 3, an optical mode coupling takes place wherein part of the energy of lightwaves traveling through the first core layer 2 shifts to the second core layer 3.

According to the second embodiment, the sensor is so structured that the surface plasmon resonance conditions at the detector 6 are not met when there is no substance to be detected at the detector 6 and the surface plasmon resonance conditions are met only when the substance to be detected is captured by the receptor adhered to the detector 6. When the surface plasmon resonance conditions are met and the substance to be detected is captured by the detector 6, part of the lightwave energy is consumed as the energy for maintaining the resonance state and the traveling-wave energy shifting to the second core layer 3 at the optical mode coupling area becomes small, thus resulting in a reduced output at the end 22.

Conventionally, a substance is detected and quantitated from the change in the absorbed amount of light or the state of surface plasmon resonance when the substance to be detected is captured by a single waveguide. With a sensor according to the present embodiment, however, a substance is detected and quantitated by the use of optical mode coupling dependent on the refractive index that changes when the substance is captured by a plurality of waveguides. This method therefore presents an advantage of analyzing minute quantities of substance with high accuracy. It can also make the equipment smaller by enabling measurement with monochromatic light. Furthermore, measurements with high S/N ratio can be obtained.

Thus, according to this embodiment, measurements with high S/N ratio can be obtained because the optical output energy from the end 22 is measured by the use of two waveguides.

The traveling-wave energy shifting from the first core layer 2 to the second core layer 3 occupies only a very small portion of the total energy of light propagated through the first core layer 2. For this reason, if the optical output energy is measured at the end 12, instead of the end 22, then it would be difficult to obtain a favorable S/N ratio. The sensor according to the present embodiment, however, employs a method of measuring at the end 22 the amount of light that has shifted to the core layer 3, so that it is possible to set the measuring range appropriately and achieve measurements at high S/N ratio using a highly sensitive receiving unit in a narrow range.

In this embodiment, as has been described above, the sensor is structured so that the receptor adhered to the detector 6 captures the substance to be detected and the surface plasmon resonance conditions are accordingly satisfied. Contrary to this, the sensor may also be structured so that the surface plasmon resonance conditions at the detector 6 collapse when the substance to be detected is captured by the receptor adhered to the detector 6. In such a case, when there is substance to be detected at the detector 6, there is more traveling-wave energy shifting to the second core layer 3 at the optical mode coupling area, thus resulting in an increased output at the end 22. In this case, too, measurements with high S/N ratio can be obtained.

According to this embodiment, performed are a step of introducing incoming light beam in the first core layer 2, a step of causing a change in the physical properties (refractive index) of the optical mode coupling area by introducing a sample in an area in contact with the first core layer 2 between the end 11 of the first core layer 2 and the optical mode coupling area, and a step of measuring the intensity of detecting light outputted from the second core layer 3. And by the measurement of the intensity of this detecting light, the presence or absence of substance to be detected in the sample is determined and, if determined present, the substance is quantitated.

Third Embodiment

A third embodiment concerns an optical waveguide sensor utilizing surface plasmon resonance and optical mode coupling, which is suited for multiple-item measurement.

Figure 5A:
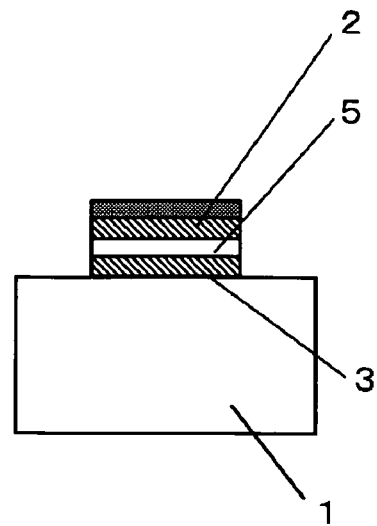
FIG. 5A and FIG. 5B illustrate schematically a structure of an optical waveguide sensor according to a third embodiment of the present invention.
Figure 5B:
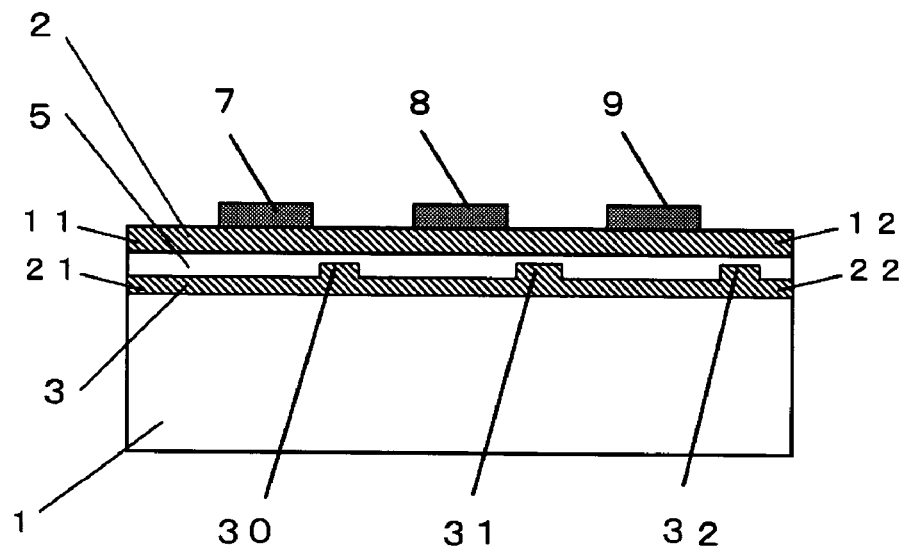

FIG. 5A and FIG. 5B illustrate schematically a structure of an optical waveguide sensor according to the third embodiment of the present invention. FIG. 5A is a cross-sectional view of the sensor, and FIG. 5B is another cross-sectional view of the sensor different from one in FIG. 5A. A second core layer 3 is disposed on the surface of a first substrate 1; a second cladding layer 5 is disposed on the surface of the second core layer 3; and a first core layer 2 is disposed on the surface of the second cladding layer 5.

A first metal thin film 7, a second metal thin film 8 and a third metal thin film 9 are disposed in parts of the surface of the first core layer 2. These metal thin films function as a detector. The first core layer 2 and the second core layer 3 are disposed counter to each other with the thin second cladding layer 5 disposed therebetween in such a manner that optical mode coupling is produced in the vicinity of each metal thin film. Those parts are called a first coupling part 30, a second coupling part 31 and a third coupling part 32.

Different receptor materials that develop interaction with different substances to be detected are placed on the surfaces of the first metal thin film 7, the second metal thin film 8 and the third metal thin film 9, respectively. This arrangement makes it possible to see which substance is reacting with which metal thin film. The materials usable as receptor materials and their fixing method are the same as described in the first embodiment.

When the lightwaves having entered the first core layer 2 from an end 11 does not develop a surface plasmon resonance with the first metal thin film 7, the lightwaves pass the first metal thin film 7 and part of the traveling-wave energy (20% for instance) shifts to the second core layer 3 at the first coupling part 30.

When the lightwaves having entered the first core layer 2 from the end 11 develops a surface plasmon resonance with the first metal thin film 7, the traveling-wave energy is transformed into resonance energy, so that the energy shifting to the second core layer 3 at the first coupling part 30.becomes nearly zero. Similarly, the amount of energy shifting to the second core layer 3 is determined at the second metal thin film 8 and the second coupling part 31 and at the third metal thin film 9 and the third coupling part 32, depending on the occurrence of surface plasmon resonance.

Thus, measurement of the energy of output light at the end 22 shows at which metal thin film (detector) a surface plasmon resonance is occurring, thus making it possible to detect and quantitate the substance or substances to be detected.

It is possible to set as appropriate the relationship between the presence/absence of substance to be detected and surface plasmon. The sensor may be structured so that the surface plasmon resonance conditions at the metal thin film 7 or the like are not met as initial conditions and the surface plasmon resonance conditions are met when the substance to be detected is captured by the metal thin film 7 or the like. Conversely, the sensor may be structured so that the surface plasmon resonance conditions at the metal thin film 7 or the like are met as initial conditions and the surface plasmon resonance conditions collapse when the substance to be detected is captured by the metal thin film 7 or the like. In either case, measurement of the energy of output light at the end 22 makes it possible to measure the substance or substances to be detected.

The sensor according to the present embodiment may make a system of measurements using either light of a single wavelength or light of a plurality of wavelengths.

Where light of a single wavelength is used, the areas of the metal thin films 7 to 9 and the intervals among the coupling parts 30 to 32 are designed appropriately, and a structure is made such that it is possible to see at which metal film an interaction between the metal thin film and the substance to be detected is taking place from the measurement of the output light energy at the end 22.

Where light of a plurality of wavelengths is used, the sensor is structured as follows. The intervals among the coupling parts 30 to 32 are designed, and the wavelengths $\lambda_1$ to $\lambda_3$ are selected, in such a manner that the shifting of light occurs only at the coupling part 30 for the incident light of $\lambda_1$, only at the coupling part 31 for the incident light of $\lambda_2$, and only at the coupling part 32 for the incident light of $\lambda_3$. With a sensor thus structured, a liquid containing a sample is first brought into contact with the metal thin films 7 to 9, and then light beams of wavelengths $\lambda_1$ to $\lambda_3$ are sent in successively and the output light energies are measured at the end 22. By obtaining the light output relative to the incident light of each wavelength, it is possible to see at which metal thin film an interaction with the substance to be detected is taking place, that is, it is possible to know the presence of any specific substance in the sample.

According to this third embodiment, the metal thin films 7 to 9 are provided, but the structure may include four or more metal films. That is, a sensor can be provided with n units of metal films so as to measure n types of substances to be detected. In such a case, a structure may be such that, on a measurement spot, m types of substances for measurement are selected from n types of substances to be detected and the sensor is adjusted accordingly. For example, the surfaces of the metal films or the sample inlets leading to the surfaces of the metal films are covered with sealing material before use of the sensor, and only when it is used, the sealing material is removed from the metal films corresponding to the m types of substances to be measured. In this manner, preparation of a single sensor can enable a variety of measurements. At the time of measurement, the metal films corresponding to substances not being measured remain sealed, so that the results of measurement with less noise may be obtained.

Fourth Embodiment

Figure 6A:
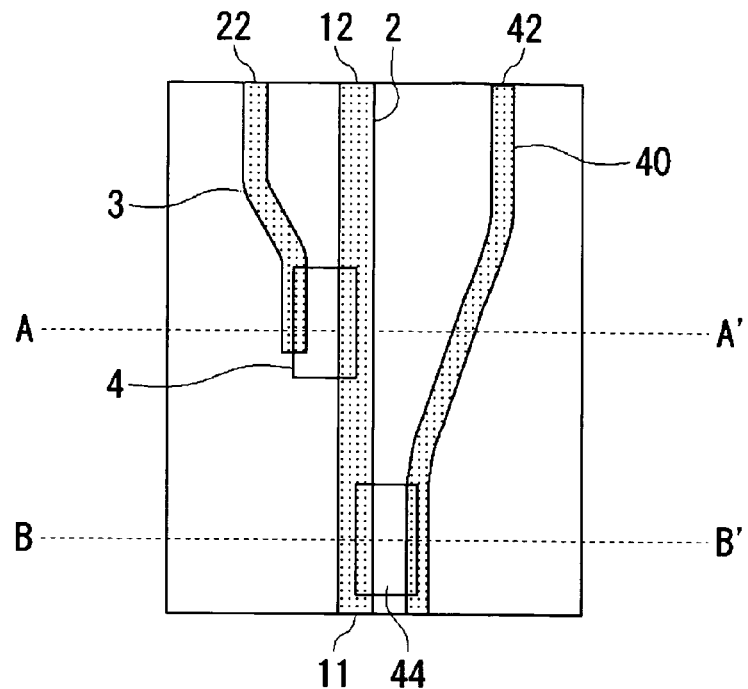
FIGS. 6A to 6C illustrate schematically a structure of a sensor according to a fourth embodiment of the present invention.
Figure 6B:
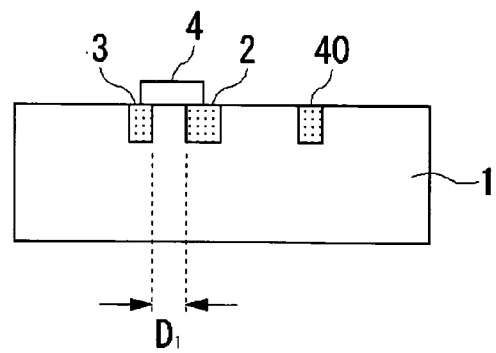
Figure 6C:
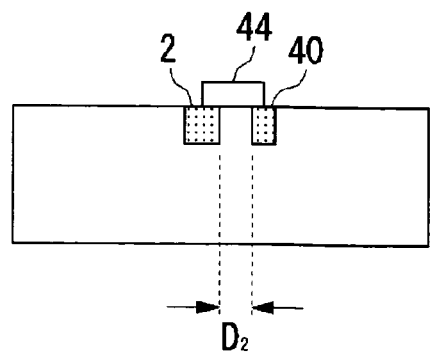

A fourth embodiment concerns a sensor for analyzing a plurality of substances at the same time. FIGS. 6A to 6C illustrate schematically a structure of a sensor according to the fourth embodiment. FIG. 6A is a top view of the sensor, FIG. 6B is an A-A' cross-sectional view of FIG. 6A, and FIG. 6C is a B-B' cross-sectional view of FIG. 6A.

Disposed on the surface of a substrate 1 are a first core layer 2, a second core layer 3 and a third core layer 40. A detector 4 is disposed on an optical coupling area where the first core layer 2 and the second core layer 3 are adjacent to each other at an interval of $D_1$. A detector 44 is disposed on an optical coupling area where the first core layer 2 and the third core layer 40 are adjacent to each other at an interval of $D_2$. The detectors 4 and 44 are the areas with predetermined receptor materials fixed on the surfaces of the substrate 1 and the first core layer 2 and the second core layer 3. In this fourth embodiment, the receptor materials used are such as to change the refractive indexes of the detectors 4 and 44 when they capture substances to be detected. The mode of capturing, which is subject to no particular limitations, may be an adsorption or a bonding. The materials utilizable as the receptor material and their fixing methods are the same as described in the first embodiment.

In this arrangement, the detectors 4 and 44 are disposed inside the same cell, and a plurality of components are measured simultaneously as a sample is led into this cell. The cell may be a fixed cell or a flow cell.

The receptor materials fixed to the detector 4 and the detector 44 react on different substances to be detected, respectively. Therefore, a plurality of substances in a sample can be determined by measuring the optical output energies at the end 22 and the end 42, respectively.

In addition to the aforementioned operations and effects, the sensor according to the fourth embodiment can perform the simultaneous measurement of a plurality of components so as to result in advantageous effects of analyzing minute quantities of a sample quickly and accurately.

Fifth Embodiment

Figure 7:
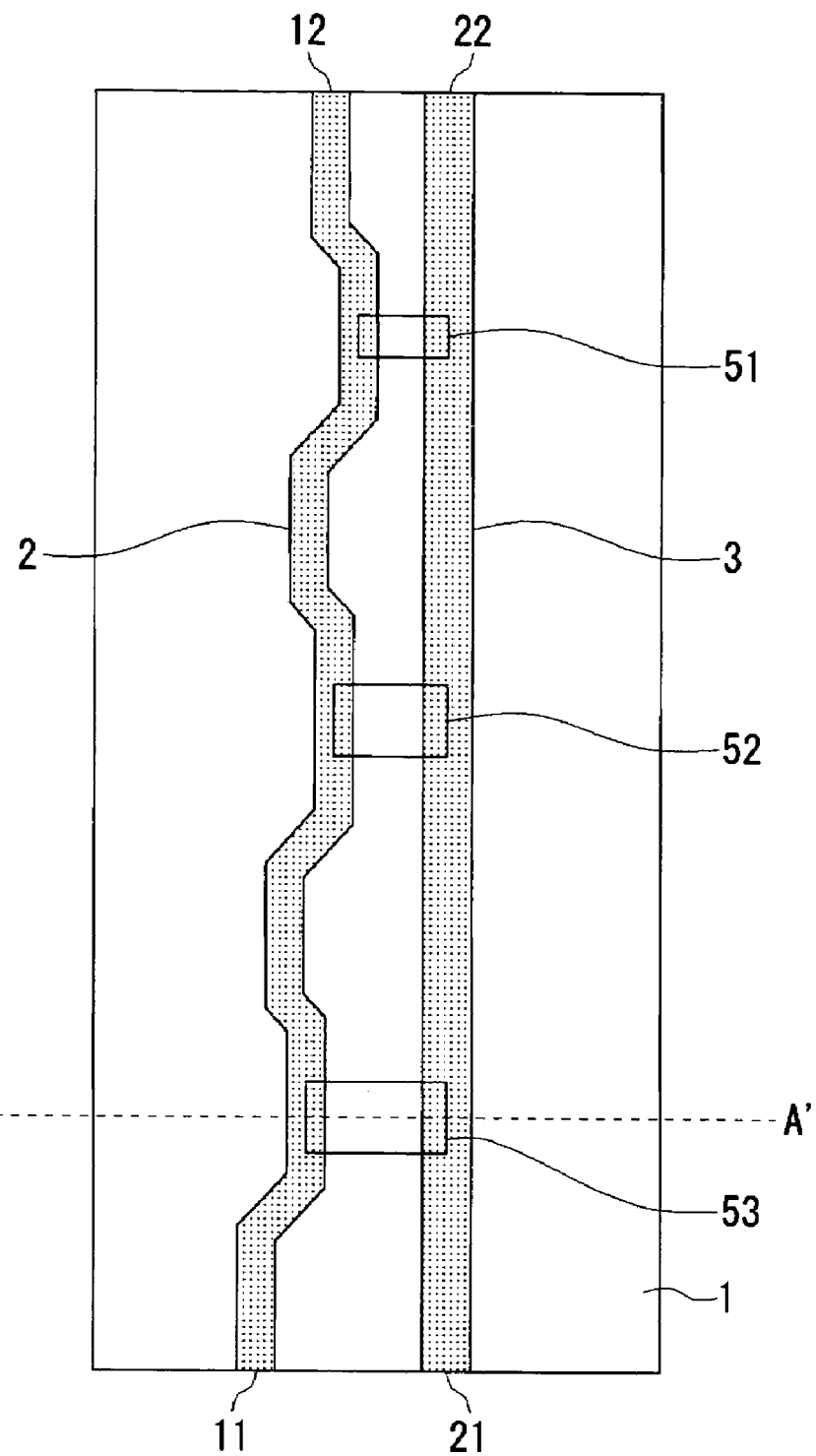
FIG. 7 illustrates a structure of an optical waveguide sensor according to a fifth embodiment of the present invention.
Figure 8:
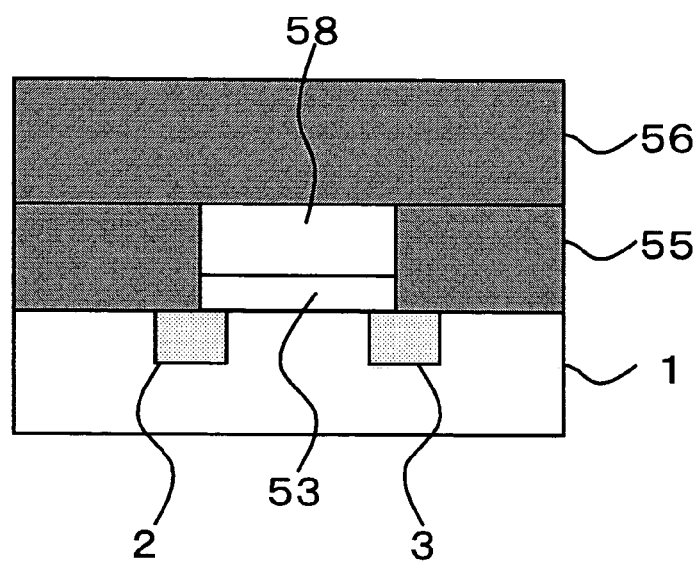
FIG. 8 illustrates a structure of an optical waveguide sensor according to a fifth embodiment of the present invention.

A fifth embodiment concerns an optical waveguide sensor utilizing surface plasmon resonance and optical mode coupling, which is suited for multiple-item measurement. FIG. 7 and FIG. 8 illustrate a structure of an optical waveguide sensor according to the fifth embodiment.

FIG. 7 is a top view of the sensor. A first core layer 2 and a second core layer 3 are disposed on the surface of a substrate 1. There are provided three optical coupling areas where the first core layer 2 and the second core layer 3 are adjacent to each other at a predetermined interval. Detectors 51, 52 and 53 are provided on the respective coupling areas. Different receptor material are fixed on the surface of the respective detectors.

FIG. 8 is an A-A' cross-sectional view of FIG. 7. The first core layer 2 and the second core layer 3 are provided on the surface of the substrate 1. A first cover member 55 and a second cover member 56 are stacked on the substrate 1 where the first cover member 55 has an opening therein. The first cover member 55 and the second cover member 56 each have a refractive index lower than that of the first core layer 2 and the second core layer 3. The detector 53 is provided on the bottom face of the opening in such a manner as to come in contact with the first core layer 2, the second core layer 3 and a region interposed between the first core layer 2 and the second core layer 3. A space above the detector 53 serves as a flow path 58.

The flow path 58 is formed in such a manner as to be parallel to the first core layer 2 and the second core layer 3, as shown in FIG. 7. And the flow path 58 is structured such that the upper surfaces of the detectors 51, 52 and 53 are exposed on the bottom face. When a sample is flowed into the flow path 58, predetermined components of the sample are selectively captured on the surfaces of the detectors 51, 52 and 53 according to its kind. As a result, a shifted amount of light from the first core layer 2 to the second core layer 3 varies. By identifying an amount of this change in the shifting, what substance to be detected is captured in which detector is known and the detection and quantitative determination of the substance can be done.

Sixth Embodiment

Figure 9:
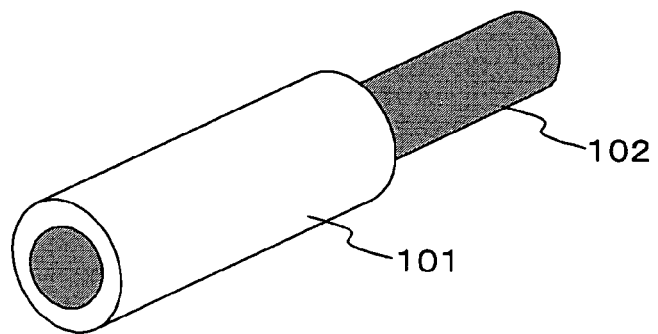
FIG. 9 shows a structure of an optical fiber used for an optical waveguide sensor according to a sixth embodiment.

In this sixth embodiment, an example of a sensor 100 using an optical fiber will be described. FIG. 9 shows a structure of an optical fiber used for a sensor according to the sixth embodiment. A structure show in FIG. 9 is such that the periphery of a core 102 having a relatively high refractive index is covered with a cladding 101 having a relatively low refractive index.

Figure 10A:
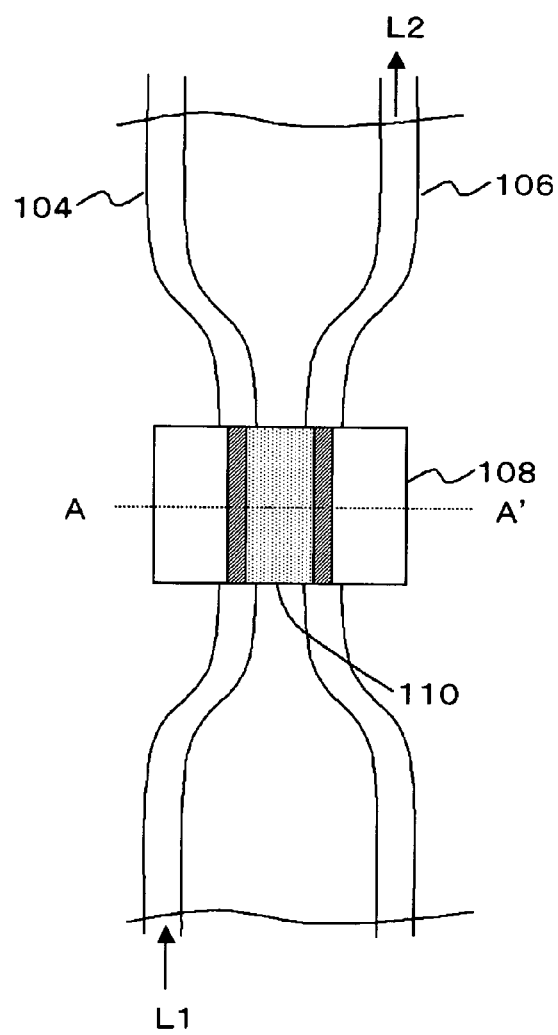
FIGS. 10A and 10B illustrate schematically a structure of an optical waveguide sensor according to a sixth embodiment.
Figure 10B:
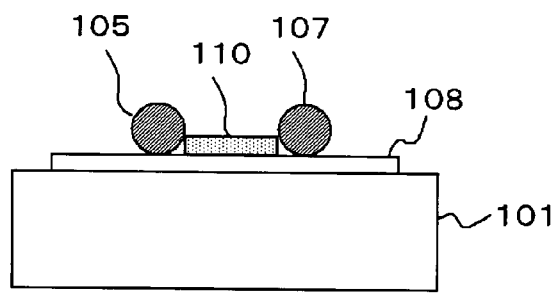

FIGS. 10A and 10B show a structure of a sensor according to the sixth embodiment. FIG. 10A is a top view of the sensor. This sensor is structured such that a first optical fiber 104 and a second optical fiber 106 are disposed parallel to each other on a substrate 101. Referring to FIG. 10A, the optical fibers are placed parallel to each other with narrower interval therebetween, compared to other areas, in an optical coupling area in the central portion. In the optical coupling area, the core of each optical fiber is exposed.

FIG. 10B is an A-A' cross-sectional view of FIG. 10A and shows a cross-sectional structure of the optical coupling area. A core 105 of the first optical fiber 104 and a core 107 of the second optical fiber 106 are fixed to the surface of a grounding member 108, and a detector 110 is provided between these cores. A receptor material, which develops an interaction with a particular substance to be detected, is fixed on the surface of the detector 110. The types of the receptor material and its fixing method are the same as described in the first embodiment and else.

Part of incoming light beam $L_1$ that has entered from an end of the first optical fiber 104 shifts, in the optical coupling area, to the second optical fiber 106 where it is observed as detecting light $L_2$ (FIG. 10A). At this time, when a predetermined substance is adhered to the detector 110, the refractive index of the detector 110 is changed, thus changing the shifted amount of light from the core 105 to the core 107 (FIG. 10B). Thereby, the substance to be detected can be analyzed. According to the sensor of the present embodiment, minute quantities of a sample can be analyzed with high accuracy.

Seventh Embodiment

Figure 11:
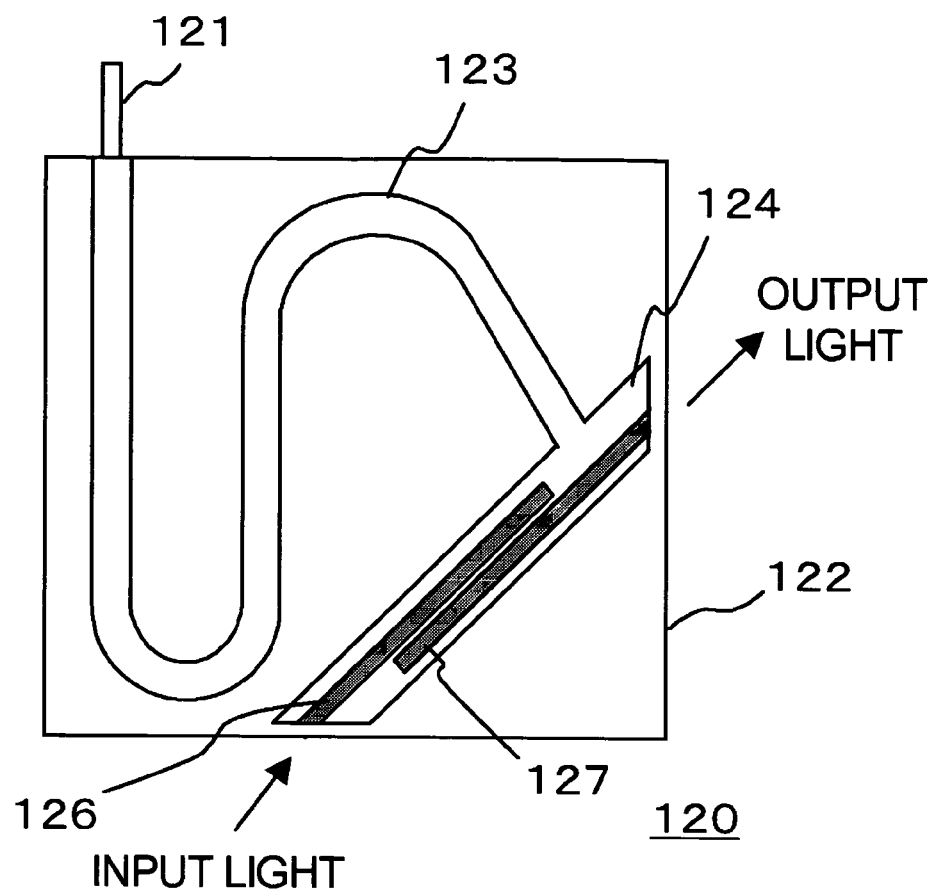
FIG. 11 illustrates schematically a structure of a measuring apparatus according to a seventh embodiment.
Figure 12A:
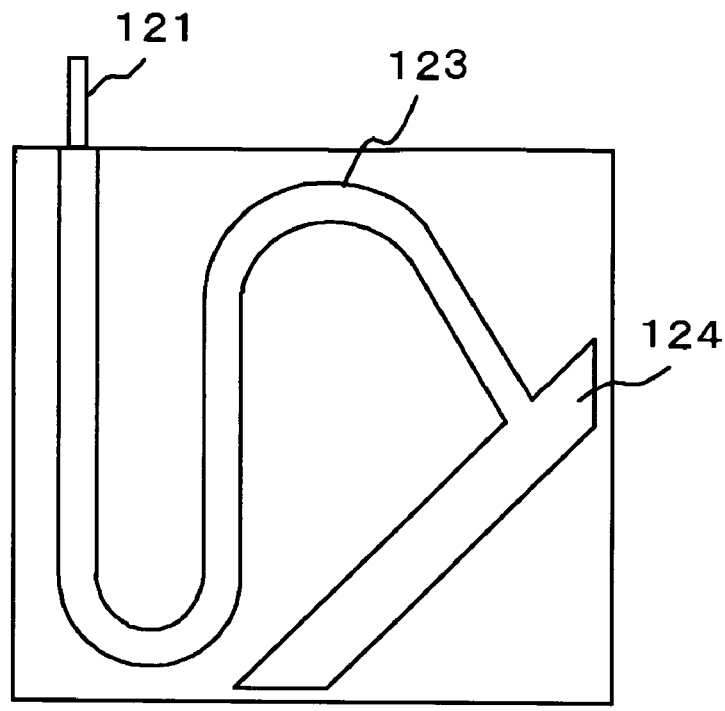
FIGS. 12A to 12C show components constituting the measuring apparatus shown in FIG. 11.
Figure 12B:
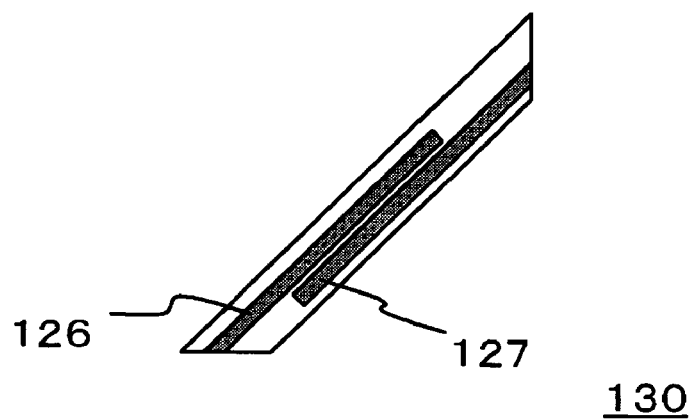
Figure 12C:
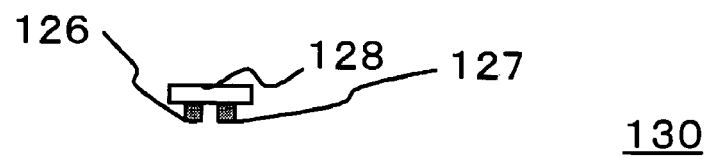

A measuring apparatus according to a seventh embodiment is so structured that bodily fluid of human or the like is collected and led into a sensor and then measured. FIG. 11 illustrates schematically a structure of a measuring apparatus 120 according to the seventh embodiment. This measuring apparatus is so structured as to be fit in a main body 122. FIGS. 12A to 12C show components constituting the measuring apparatus shown in FIG. 11. This measuring apparatus is comprised of a main body 122 shown in FIG. 12A and a sensor 130 shown in FIGS. 12B and 12C. The sensor 130 is structured in a manner such that it is detachable from the main body 122. Thus, the type of the sensor is selected to suit the measurement purpose, so that the selected sensor can be attached to the main body 122. Though, in this example, the sensor 130 is fit in a recess provided in the main body 122, the structure therefor is not limited thereto and various other structures may be adopted. For example, a structure may be such that a groove portion is provided in the main body 122 and the sensor 130 is inserted sideways in a sliding manner.

Figure 14A:
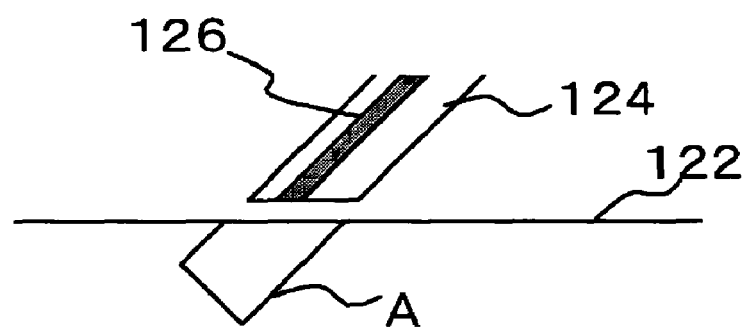
FIGS. 14A and 14B are provided for the explanation of a structure of a waveguide connecting portion.
Figure 14B:
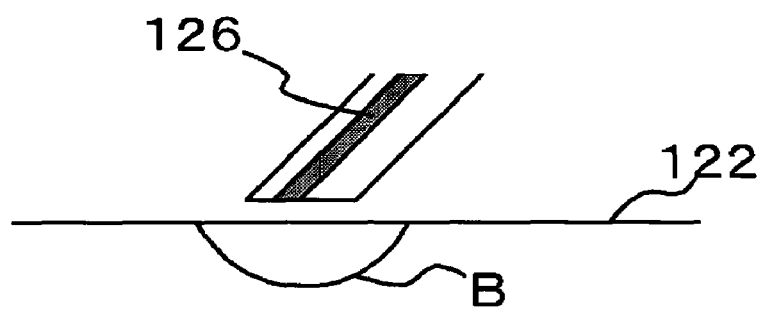

Referring to FIG. 11, the light source is connected to an inlet end of a first waveguide 126. A receiving unit is connected to an exit end of a second waveguide 127. As the light source, a semiconductor laser is used whereas a silicone photodiode is used as the receiving unit. As shown in FIG. 14A, in order to efficiently guide the light into the first waveguide 126 a waveguide A is provided at an edge. As shown in FIG. 14B, a lens B may be added in place of the waveguide A. The lens B may be called a prism. In this manner, input light can be efficiently led to the first waveguide 126 while the loss of light is suppressed. It is to be noted that material used for the waveguide A and the les B are not particularly limited to any specific material. However, the same kind of material as the main body 122 may be used, so that the waveguide A and the lens B can be produced simultaneously when the main body is formed.

The main body 122 is produced by a technique such as injection molding, using thermoplastic resin. In the present embodiment, the main body is made of polyethylene terephthalate. The size thereof is, for example, 20 mm×20 mm.

Any sensor structured as in the previous embodiments may be used here as the sensor 130. Here, a sensor whose structure is similar to that described in the first embodiment (FIGS. 1A and 1B) will be used. The sensor 130 is structured such that there are provided therein a first waveguide 126 where the incoming light beam is led to a lid portion 128 that plays a role of the cladding and a second waveguide 127 from which detecting light is extracted and they are separated, with a distance therebetween, from each other. The first waveguide 126 and the second waveguide 127 are constituted by material having a higher refractive index than the lid portion 128, blood and the like.

A receptor material in which a predetermined constituent in the blood is absorbed or combined is placed on the detector 4 (FIGS. 1A and 1B) inside the sensor 130.

A method for using the apparatus shown in FIG. 11 will be described with reference to an example where blood is a specimen. The blood is injected from a needle 121 which serves as a bodily fluid collecting unit. The injected blood is centrifuged or mixed with a reagent, and is then led to the detector 4 inside the sensor 130 via a flow path 123. The blood that has been led to the detector 4 is measured following the principle of operation described in the first embodiment and a targeted constituent is quantitated. That is, as shown in FIG. 11, the incoming light beam is led to the first waveguide 126 and the detecting light is extracted from the second waveguide 127. Measuring the energy of this detecting light can achieve quantitating the targeted constituent.

According to the present embodiment, the bodily fluid is collected and measured by the same apparatus, thus realizing quick measurement. Besides, the collected blood is measured at once, so that accurate measurement results can be obtained. Moreover, since the sensor is detachable from the main body, it can be used for various purposes of measurement.

Embodiment 1

Using the sensor similarly structured according to the above generic first embodiment, actual measurement was carried out in this actual Embodiment 1.

A sensor according to Embodiment 1 is manufactured as follows. PMMA (polymethylmethacrylate) is adopted as material for the core layer. A substrate, made of PMMA, whose thickness is 1 mm (refractive index: 1.49) is covered with a mask over a portion that forms the first core layer 2 and the second core layer 3. The width of the first core layer and the second core layer 3 is 1 μm and the length thereof is 30 mm. The minimum distance between the first core layer 2 and the second core layer 3 is 0.5 μm.

The area which is not covered by the mask is removed by etching by 1 μm in depth. Acrylic resin (refractive index: 1.33) which will form as a substrate 1 is pressed thereon while heating it. Thereafter, the surface of PMMA is polished. As a result, the first core layer 2 and the second core layer 3, which are covered with the substrate 1, can be obtained.

As a detector 4, avidin is fixed on dextran in the intermediate area between the first core layer 2 and the second core layer 3. While the laser beam of wavelength 670 nm is being sent in from the end 11, solution that contains biotin serving as substance to be detected is dropped on the detector 4 and then the output light from the end 22 is measured.

Figure 13:
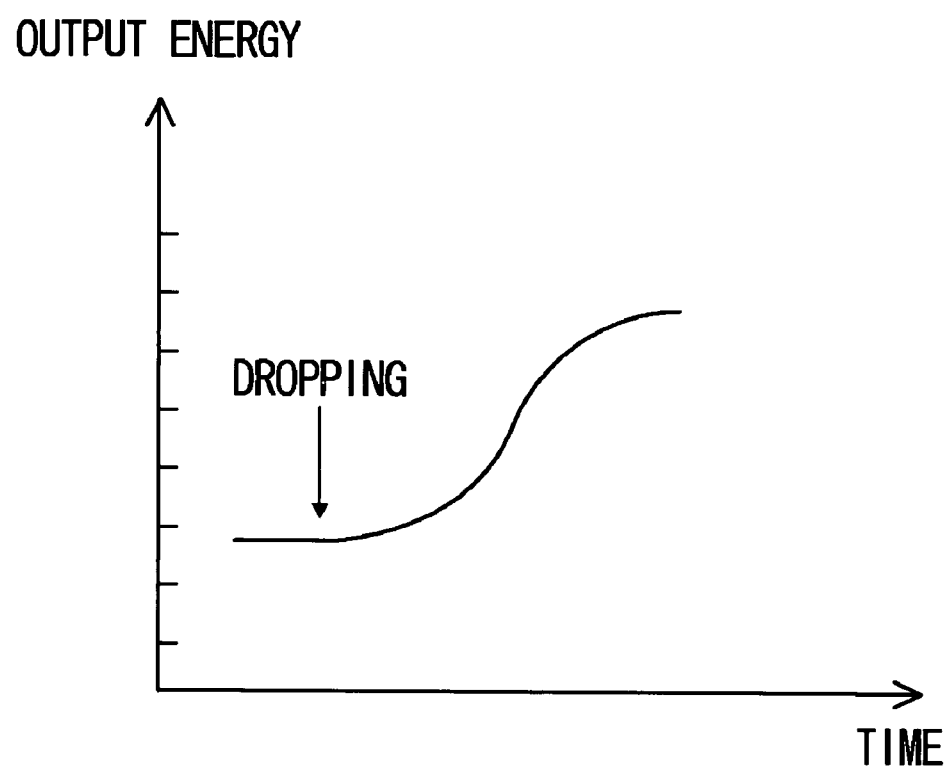
FIG. 13 shows the measurement results in Embodiment 1.

FIG. 13 shows the measurement results. Referring to FIG. 13, as the detector captures the substance to be detected, the output light energy at the end 22 becomes larger. With these varied values, the presence or absence, the type and the amount of the substance to be detected can be analyzed.

Embodiment 2

In this actual Embodiment 2, actual measurement was carried out using the sensor similarly structured according to the above generic first embodiment. The measurement conditions are as follow.

Wavelength of incoming light beam: 1.55 μm.
Refractive index of the first core: 1.5.
Refractive index of the second core: 1.5.
Refractive index of the substrate: 1.49.
Interval between cores: 2.4 μm.
Propagation angle of waveguide mode: 3.01 deg.
Length of reaction area: This is set in such a manner that the energy transfers 100% from the first core to the second core when the refractive index is 1.33.

Figure 15:
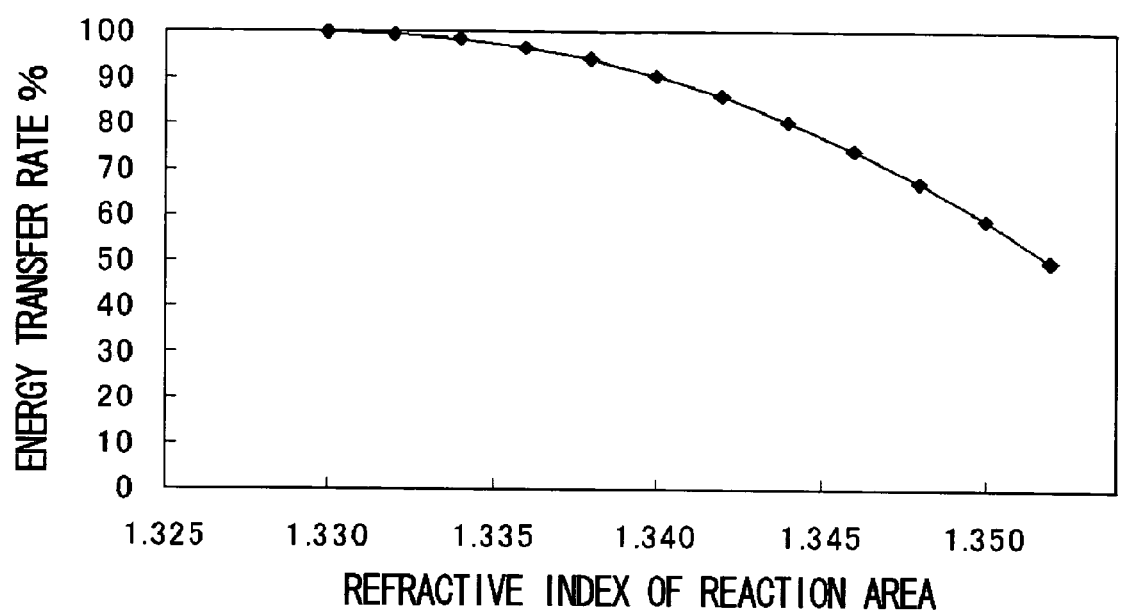
FIG. 15 shows the measurement results in Embodiment 2.

FIG. 15 shows the measurement results. In FIG. 15, the horizontal axis in this graph indicates the refractive index of the reaction area (it is sequentially increased from the refractive index of 1.33 of water) whereas the vertical axis in the graph indicates the energy transfer rate of lightwaves from the first core to the second core. According to this graph, the energy transfer rate decreases as the refractive index of reaction area becomes larger.

The variation of 0.001 in refractive index corresponds to adhesion of protein on the surface by 1 ng/mm$^2$. The actual resolution of a conventional SPR sensor is 10 ng/mm$^2$, which corresponds to the variation of 0.01, which, in turn, corresponds to the change of 10% in the intensity of output light beam according to this graph (in the case when the refractive index changes from 1.33 to 1.34). As is obvious from the above and the graph, the sensor according to the present embodiment can achieve significantly high measurement sensitivity compared to the conventional SPR sensor.

The present invention has been described based on the embodiments which are only exemplary. It is understood by those skilled in the art that there exists other various modifications to the combination of each component and process described above and those such modifications are encompassed by the scope of the present invention which is defined by the appended claims.

What is claimed is:
1. An optical waveguide sensor, comprising:
   a first waveguide having an inlet end for incoming light;
   a second waveguide having an exit end for detecting light;
   an optical coupling area where said first waveguide and said second waveguide are positioned with a predetermined interval therebetween; and
   a detector, interacting with a substance to be detected, which is positioned in the close proximity of said first waveguide and is located within an area covered from the inlet end up to the optical coupling area;
   wherein the detector includes metal film.
2. An optical waveguide sensor according to claim 1, wherein a receptor material, which captures selectively a substance to be detected, is placed on a surface of the detector.

3. An optical waveguide sensor according to claim 1, wherein there are provided a plurality of detectors and a plurality of different receptor materials are placed on the respective plurality of detectors.

4. An optical waveguide sensor according to claim 1, wherein there is provided a flow path in contact with the detector and wherein a surface of the detector is exposed on the flow path.

5. A measuring apparatus for detecting a substance in a bodily fluid, comprising:
   a bodily fluid collecting unit;
   a sensor which analyzes bodily fluid collected by said bodily fluid collecting unit; and
   a flow path which introduces the bodily fluid from said bodily fluid collecting unit to said sensor,
   wherein said sensor comprises:
   a first waveguide having an inlet end for incoming light;
   a second waveguide having an exit end for detecting light;
   an optical coupling area where said first waveguide and said second waveguide are positioned with a predetermined interval therebetween; and
   a detector, interacting with a substance to be detected, which is positioned in the close proximity of the first waveguide and is located within an area covered from the inlet end up to the optical coupling area,
   wherein said flow path is structured such that the bodily fluid is led to a detector included in said sensor; and
   wherein the detector includes metal film.

6. A measuring method for use with a sensor having a first waveguide, a second waveguide and an optical coupling area where said first waveguide and said second waveguide are positioned with a predetermined interval therebetween, the method comprising:
   introducing incoming light in the first waveguide;
   introducing a sample, in an area in contact with the first waveguide between an introducing end of the incoming light and the optical coupling area, to cause a change in a physical property of the optical coupling area by interacting with a detector comprising a metal film;
   measuring the intensity of detecting light outputted from the second waveguide; and
   detecting the presence or absence of a substance to be detected or quantitating the substance by said measuring.

7. A measuring method according to claim 6, wherein the physical property of the optical coupling area is refractive index.

8. An optical waveguide sensor for detecting a substance, comprising:
   a second core layer comprising an exit end for detecting light;
   a cladding layer disposed on the surface of the second core layer;
   a first core layer comprising an inlet end for incoming light, the first core layer being disposed on the surface of the cladding layer such that the cladding layer is interposed between the first core layer and the second core layer;
   at least one thin metal film disposed on the surface of the first core layer, such that the first core layer is interposed between the at least one thin metal film and the cladding layer;
   wherein the first core layer and the second core layer are configured such that optical mode coupling occurs in an optical coupling region located proximate to each of the at least one thin metal film.

9. The optical waveguide sensor of claim 8, wherein the at least one thin metal film comprises a plurality of thin metal films.

10. An optical waveguide sensor for detecting a plurality of substances, comprising:
    a first waveguide comprising an inlet end for incoming light;
    a second waveguide comprising an exit end for detecting light;
    a third waveguide comprising an exit end for detecting light;
    a first optical coupling area where said first waveguide and said second waveguide are positioned with a first predetermined interval therebetween;
    a second optical coupling area where said first waveguide and said third waveguide are positioned with a second predetermined interval therebetween;
    a first detector disposed in the first optical coupling area, the first detector being configured to interact with one of the plurality of substances to be detected; and
    a second detector disposed in the second optical coupling area, the second detectors being configured to interact with one of the plurality of substances to be detected.

11. An optical waveguide sensor for detecting a plurality of substances, comprising:
    a first waveguide having an inlet end for incoming light;
    a second waveguide having an exit end for detecting light; and
    a plurality of optical coupling areas where said first waveguide and said second waveguide are positioned with a predetermined interval therebetween;
    a plurality of detectors, the plurality of detectors configured such that in at least two of said plurality of optical coupling areas there is provided one of the plurality of detectors disposed between said first waveguide and said second waveguide, the one of the plurality of detectors being configured to interact with one of the plurality of substances to be detected.

12. The optical waveguide sensor of claim 11, wherein the plurality of optical coupling areas where said first waveguide and said second waveguide are positioned with a predetermined interval therebetween further comprises:
    a first optical coupling area where said first waveguide and said second waveguide are positioned with a first predetermined interval therebetween; and
    a second optical coupling area where said first waveguide and said second waveguide are positioned with a second predetermined interval therebetween;
    wherein the first predetermined interval and the second predetermined interval are non-equal.

13. The optical waveguide sensor of claim 11, wherein a plurality of different receptor materials which selectively captures the plurality of substances to be detected is disposed on a surface of each of the plurality of detectors.

14. The optical waveguide sensor of claim 11, wherein there is provided a flow path in contact with at least one of the plurality of detectors and wherein a surface of the at least one of the plurality of detectors is exposed on the flow path.

15. An optical waveguide sensor for detecting a substance, comprising:
    a first optical fiber having a core;
    a second optical fiber having a core;
    a grounding member;
    a detector; and
    an optical coupling area where the first optical fiber and the second optical fiber are positioned with a predetermined interval therebetween; wherein the core of the first optical fiber and the core of the second optical fiber are exposed in the optical coupling area;

the core of the first optical fiber and the core of the second optical fiber are fixed to a surface of the grounding member; and the detector is positioned between the core of the first optical fiber and the core of the second optical fiber in the optical coupling area.

* * * * *